United States Patent
Thomas

(10) Patent No.: US 8,424,183 B2
(45) Date of Patent: Apr. 23, 2013

(54) POROUS TITANIUM FEMORAL SLEEVES AND THEIR USE IN REVISION KNEE SURGERY

(75) Inventor: Kyle Thomas, Fort Wayne, IN (US)

(73) Assignee: DePuy Synthes Products, LLC, Raynham, MA (US)

(*) Notice: Subject to any disclaimer, the term of this patent is extended or adjusted under 35 U.S.C. 154(b) by 513 days.

(21) Appl. No.: 12/476,648

(22) Filed: Jun. 2, 2009

(65) Prior Publication Data
US 2010/0076565 A1    Mar. 25, 2010

Related U.S. Application Data

(60) Provisional application No. 61/058,254, filed on Jun. 3, 2008.

(51) Int. Cl.
*B21D 39/00* (2006.01)
*A61F 2/38* (2006.01)

(52) U.S. Cl.
USPC .................................. 29/428; 623/20.16

(58) Field of Classification Search .............. 29/17.2, 29/428, 898; 156/60; 623/20.16; 606/86 R
See application file for complete search history.

(56) References Cited

U.S. PATENT DOCUMENTS

| | | | |
|---|---|---|---|
| 2,947,308 A | 8/1960 | Gorman | |
| 4,136,405 A | 1/1979 | Pastrick et al. | |
| 4,523,587 A | 6/1985 | Frey | |
| 4,549,319 A | 10/1985 | Meyer | |
| 4,634,444 A | 1/1987 | Noiles | |
| 4,659,331 A | 4/1987 | Matthews et al. | |
| 4,711,639 A | 12/1987 | Grundei | |
| 4,790,852 A | 12/1988 | Noiles | |
| 4,822,366 A | 4/1989 | Bolesky | |
| 4,827,919 A | 5/1989 | Barbarito et al. | |
| 4,846,839 A | 7/1989 | Noiles | |
| 4,883,488 A | 11/1989 | Bloebaum et al. | |
| 4,888,021 A | 12/1989 | Forte et al. | |
| 4,944,757 A | 7/1990 | Martinez et al. | |
| 5,011,496 A | 4/1991 | Forte et al. | |
| 5,133,760 A | 7/1992 | Petersen et al. | |
| 5,152,796 A | 10/1992 | Slamin | |
| 5,197,488 A | 3/1993 | Kovacevic | |
| 5,211,664 A | 5/1993 | Tepic et al. | |

(Continued)

FOREIGN PATENT DOCUMENTS

| | | | |
|---|---|---|---|
| EP | 1004283 B1 | 5/2005 | |
| EP | 1532945 A2 | 5/2005 | |

(Continued)

OTHER PUBLICATIONS

European Search Report, European Application No. 11178524.2-2310, dated Nov. 15, 2011, 5 pages.

(Continued)

*Primary Examiner* — Alexander P Taousakis
(74) *Attorney, Agent, or Firm* — Barnes & Thornburg LLP

(57) ABSTRACT

The invention concerns monolithic foam sleeves that comprises titanium or titanium alloy foam having a porosity of 50 to 85% and possess a proximal end, a distal end, an interior wall that defines an interior channel and extends from the proximal end to the distal end; and a terraced outer surface that tapers such that said sleeve is widest at the distal end and most narrow at the proximal end.

4 Claims, 14 Drawing Sheets

U.S. PATENT DOCUMENTS

| | | | |
|---|---|---|---|
| 5,326,359 | A | 7/1994 | Oudard |
| 5,358,530 | A | 10/1994 | Hodorek |
| 5,387,241 | A | 2/1995 | Hayes |
| 5,405,395 | A | 4/1995 | Coates |
| 5,413,604 | A | 5/1995 | Hodge |
| 5,462,550 | A * | 10/1995 | Dietz et al. .................. 606/86 R |
| 5,462,563 | A | 10/1995 | Shearer et al. |
| 5,480,445 | A | 1/1996 | Burkinshaw |
| 5,683,467 | A | 11/1997 | Pappas |
| 5,716,412 | A * | 2/1998 | DeCarlo et al. .............. 623/23.5 |
| 5,766,256 | A | 6/1998 | Oudard et al. |
| 5,782,921 | A | 7/1998 | Colleran et al. |
| 5,824,103 | A | 10/1998 | Williams |
| 5,871,548 | A | 2/1999 | Sanders et al. |
| 5,957,979 | A | 9/1999 | Beckman et al. |
| 5,997,581 | A | 12/1999 | Khalili |
| 6,039,764 | A | 3/2000 | Pottenger et al. |
| 6,074,423 | A | 6/2000 | Lawson |
| 6,074,424 | A | 6/2000 | Perrone et al. |
| 6,080,195 | A | 6/2000 | Colleran et al. |
| 6,136,029 | A | 10/2000 | Johnson et al. |
| 6,162,254 | A | 12/2000 | Timoteo |
| 6,312,473 | B1 * | 11/2001 | Oshida ....................... 623/23.55 |
| 6,423,096 | B1 | 7/2002 | Musset et al. |
| 6,613,092 | B1 | 9/2003 | Kana et al. |
| 6,843,806 | B2 | 1/2005 | Hayes et al. |
| 6,946,001 | B2 | 9/2005 | Sanford et al. |
| 6,981,991 | B2 | 1/2006 | Ferree |
| 7,105,026 | B2 | 9/2006 | Johnson et al. |
| 7,179,295 | B2 | 2/2007 | Kovacevic |
| 2003/0065397 | A1 | 4/2003 | Hanssen et al. |
| 2003/0153981 | A1 | 8/2003 | Wang et al. |
| 2003/0183025 | A1 | 10/2003 | Krstic |
| 2004/0049284 | A1 | 3/2004 | German et al. |
| 2004/0117024 | A1 | 6/2004 | Gerbec et al. |
| 2004/0162619 | A1 | 8/2004 | Blaylock et al. |
| 2004/0172137 | A1 | 9/2004 | Blaylock et al. |
| 2004/0236424 | A1 | 11/2004 | Berez et al. |
| 2005/0042288 | A1 | 2/2005 | Koblish et al. |
| 2005/0246021 | A1 | 11/2005 | Ringeisen et al. |
| 2005/0249625 | A1 | 11/2005 | Bram et al. |
| 2005/0278034 | A1 | 12/2005 | Johnson et al. |
| 2007/0088443 | A1 | 4/2007 | Hanssen et al. |
| 2008/0021566 | A1 | 1/2008 | Peters et al. |

FOREIGN PATENT DOCUMENTS

| | | | |
|---|---|---|---|
| EP | 1570812 | A1 | 9/2005 |
| FR | 2772593 | | 6/1999 |
| WO | WO 8302555 | A1 | 8/1983 |
| WO | WO 0205732 | A1 | 1/2002 |
| WO | WO 03101647 | A2 | 12/2003 |
| WO | WO 2005107829 | A2 | 11/2005 |
| WO | WO 2006014294 | A1 | 2/2006 |
| WO | WO 2007097949 | A2 | 8/2007 |

OTHER PUBLICATIONS

A. Laptev et al., Study of Production Route for Titanium Parts Combining Very High Porosity and Complex Shape, Power Metallurgy, 2004, 8 pages, vol. 47 No. 1.

* cited by examiner

POROUS TITANIUM FEMORAL SLEEVES AND THEIR USE IN REVISION KNEE SURGERY

RELATED APPLICATIONS

This application claims priority to U.S. Patent Application No. 61/058,254, filed Jun. 3, 2008, the disclosure of which is incorporated herein in its entirety.

TECHNICAL FIELD

The invention concerns, inter alia., porous titanium femoral sleeves and their use in revision knee surgery.

BACKGROUND

Typical knee prostheses include a tibial component, a femoral component, and a patellar component. The femoral component generally includes a pair of spaced apart condylar portions, the superior surfaces of which articulate with a portion of the tibial component. A femoral stem assembly, used to provide stability to the replaced knee joint, seats within the medullary canal of a distal portion of a femur, and is typically coupled to the femoral component by specialized coupling devices, such as a collar and bolt. Some prosthetic knee joints include a structure known as a Morse taper post that extends from the inferior surface of the femoral component to mate with a femoral sleeve that is securable to the femoral stem assembly. The femoral component may include a boss having a slot for receiving the components of the modular junction.

Knee replacement surgery requires the replacement of the distal end of the femur and the proximal end of the tibia. Implant loosening, infection, and device wear are well-documented failure modes of primary knee arthroplasty. In cases where the primary implants fail, a secondary operation is required to replace the faulty device. The factors associated with device failure, including infection and osteolysis, often lead to a deterioration of bone quality in proximity to the implanted knee replacement devices. Upon removal of the faulty device, large bone defects are often encountered on both the tibia and the femur. These defects are often characterized by large cavitary voids along with cortical rim defects. Traditionally, treatment of these defects required the removal of a large amount of stable cortical bone to facilitate the implantation of a metal replacement for the bone defect.

Revision knee arthroplasty has existed since the first primary knees failed and the problem encountered due to bone loss upon revision is therefore not a new problem. Noiles et. al., U.S. Pat. No. 4,846,839 ("the 839 patent"), disclose a method for affixing a prosthesis to bone that incorporates flanges being placed on the femoral stem conforming to the anatomy of the femoral canal. The geometry of the device transfers stresses to the bone in a manner that generally corresponds to the types of stress transfers that occur in natural bone. The prior art also mentions coating or roughened surfaces that could be applied to stepped tibial sleeves to improve fixation with the bone.

Blaylock et al., U.S. Published Patent Application No. 200410162619 ("the 619 application"), describe a femoral augment system to replace bone defects as described in US 200410172137. The proposed invention incorporates U-shaped augments made of a highly porous tantalum material. The intent of the device is said to be minimization of bone loss while providing a stable basis for a femoral implant. The device, however, does not incorporate the stepped design and therefore does not optimally transfer stress from the implant to the bone. The device also does not contain a means for mechanically fixing the femur to the femoral augment. The femur must be cemented to the femoral augment that provides for a decreased rotational stability compared to a mechanical lock.

While much research has been invested into devices that can be used when a primary knee implant fails, there are still important improvements that are needed. Areas of needed improvements include improved transfer of stresses to the bone in a manner that generally corresponds to the types of stress transfers that occur in natural bone and improved rotational stability.

SUMMARY

One aspect of the invention concerns monolithic foam sleeves that comprise titanium or titanium alloy foam having a porosity of 50 to 85% and possesses
- a proximal end,
- a distal end,
- an interior wall that defines an interior channel and extends from the proximal end to the distal end; and
- a terraced outer surface that tapers such that said sleeve is widest at the distal end and most narrow at the proximal end.

In some preferred embodiments, the sleeve is constructed of a material that has a porosity of 60 to 80%. In certain sleeves, the titanium alloy is Ti6Al4V. In some embodiments, commercially pure titanium (CP titanium) is used to construct the foam sleeve.

The sleeves can have a substantially circular cut to account for the inter-condylar notch present at the distal posterior aspect of the femur.

The shape and size of the terraced outer surface can generally correspond to the shape the distal end of the femur of a mammal. In some embodiments, the terraced outer surface's most distal layers are substantially rectangular and become increasingly circular proximally.

In certain embodiments, the terraced outer surface's most distal layers are substantially polygonal in shape and become increasingly circular proximally. In some preferred embodiments, the polygon is simple (i.e., does not cross itself) and may be convex (i.e., any line that is drawn through the polygon (not tangent to an edge or corner) meets the boundary exactly two times).

In certain embodiments, the sleeve additionally comprises a distal notch.

Certain sleeves have the additional feature of an adapter that is affixed to the interior channel of the sleeve at the distal end of said sleeve, has a channel in communication with the interior channel of the sleeve; and an exterior geometry generally corresponding to the shape of the interior channel of the sleeve. In some embodiments, the channel in the adaptor is offset in the medial/lateral plane or the anterior/posterior plane by a distance between 2 mm and 8 mm relative to the center of the interior channel of the sleeve.

Another feature that can be present in the sleeves of the instant invention are one or more titanium inserts that have a porosity of less than 10% and is positioned within said sleeve such that a portion of said insert is exposed within said outer surface. Such inserts can provide an area of increased strength that is useful, for example, in accommodating a screw or other attachment hardware.

Other aspects of the invention concern methods of forming femur implants comprising joining the femoral sleeve to the femoral component, where the femur sleeve comprises titanium or titanium alloy foam having a porosity of 50 to 85% and possesses a proximal end,
    a distal end,
    an interior wall that defines an interior channel and extends from the proximal end to the distal end; and
    a terraced outer surface that tapers such that said sleeve is widest at the distal end and most narrow at the proximal end.

Yet other aspects of the invention concern methods of replacing a knee prosthesis device comprising inserting a prosthesis device to the cancellous region of a femur, said device having a sleeve, said femur sleeve comprising titanium or titanium alloy foam having a porosity of 50 to 85% and possesses a proximal end,
    a distal end,
    an interior wall that defines an interior channel and extends from the proximal end to the distal end; and
    a terraced outer surface that tapers such that said sleeve is widest at the distal end and most narrow at the proximal end.

DETAILED DESCRIPTION OF ILLUSTRATIVE EMBODIMENTS

In a revision knee surgery, establishing a stable femoral base is critical to long-term implant survivorship. The present invention provides femoral implant devices that can be used to fill cavitary femoral defects and establish a stable femoral plateau without sacrificing healthy bone. The devices are made of a highly porous titanium structure that facilitates bone ingrowth. In addition, the devices provide a stable basis for replacement femoral components to be fixed to definitively through mechanical interlock or cementation.

The present invention includes a family of femoral sleeves based upon the design of the S-ROM femoral sleeves. The basic sleeve geometry is described by Noiles et. al. in U.S. Pat. No. 4,846,839. Unlike the prior art sleeves, the sleeves of the instant invention are made of a highly porous titanium material that has a high coefficient of friction on the exterior bone-contacting surface to encourage bone ingrowth. The internal surface of the sleeve is smooth and provides a substrate for cementation of a femur or permanent fixation of a femoral taper adapter. The femoral taper adapter can be permanently fixed to the porous titanium sleeve through a sintering process. The adapter has an exterior geometry designed to match the interior geometry of the sleeve and an interior geometry to mate with the femoral taper adapter. The adapter provides a means for mechanically fixing the femoral sleeve to the femur.

Figure 1:
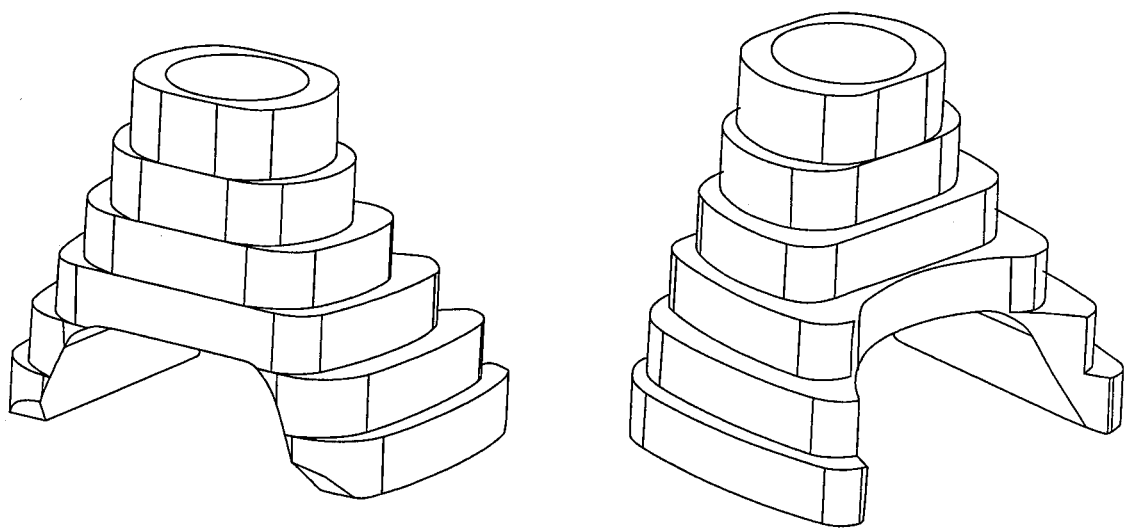
FIG. 1 presents an example of a femoral sleeve.
Figure 2:
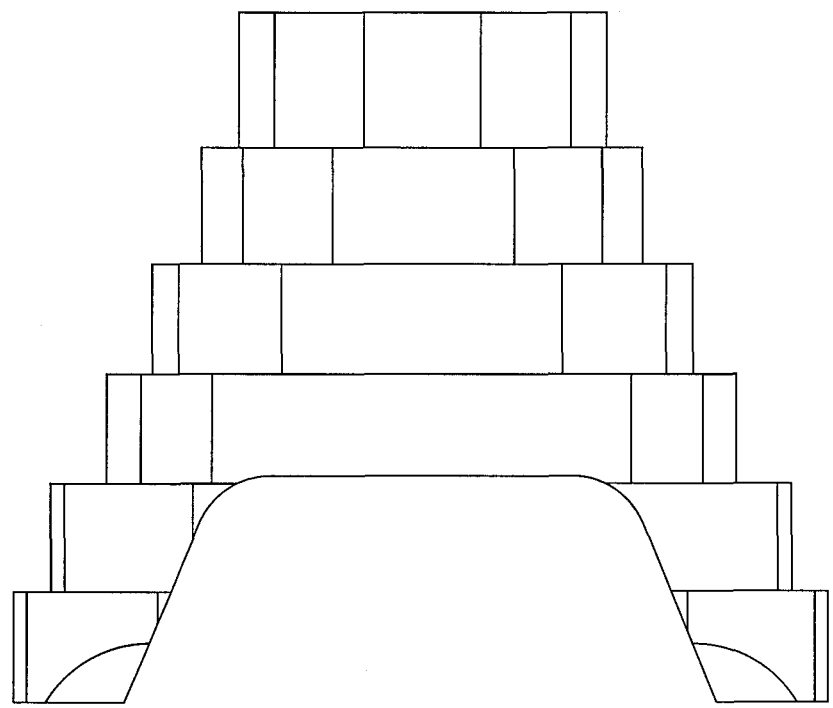
FIG. 2 presents a front view of a femoral sleeve.
Figure 3:
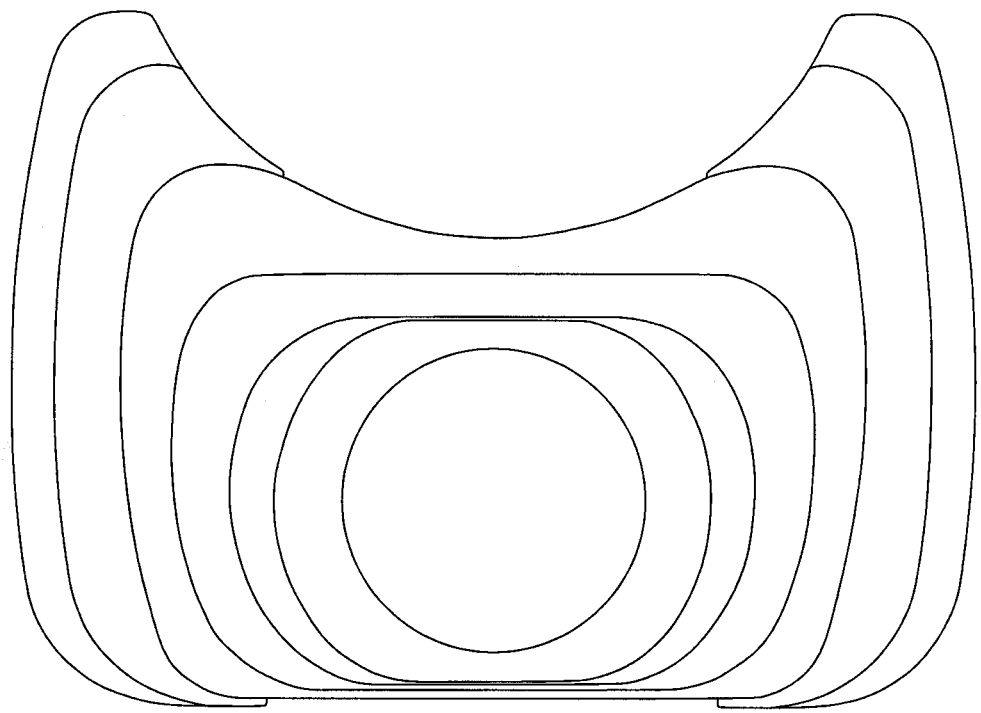
FIG. 3 presents a top view of a femoral sleeve.

The base component of the system is the porous titanium sleeve with the stress transferring steps as shown in FIG. 1. A front view and top view of the sleeve are shown in FIGS. 2 and 3 respectively. Unlike prior devices, the sleeves of the present invention are made of a highly porous titanium material that has a high coefficient of friction on the exterior bone-contacting surface to encourage bone ingrowth. By using a material that is highly porous throughout, bone growth is encouraged in a manner substantially greater to any coating or roughened surface finish mentioned in the prior art.

Figure 4:
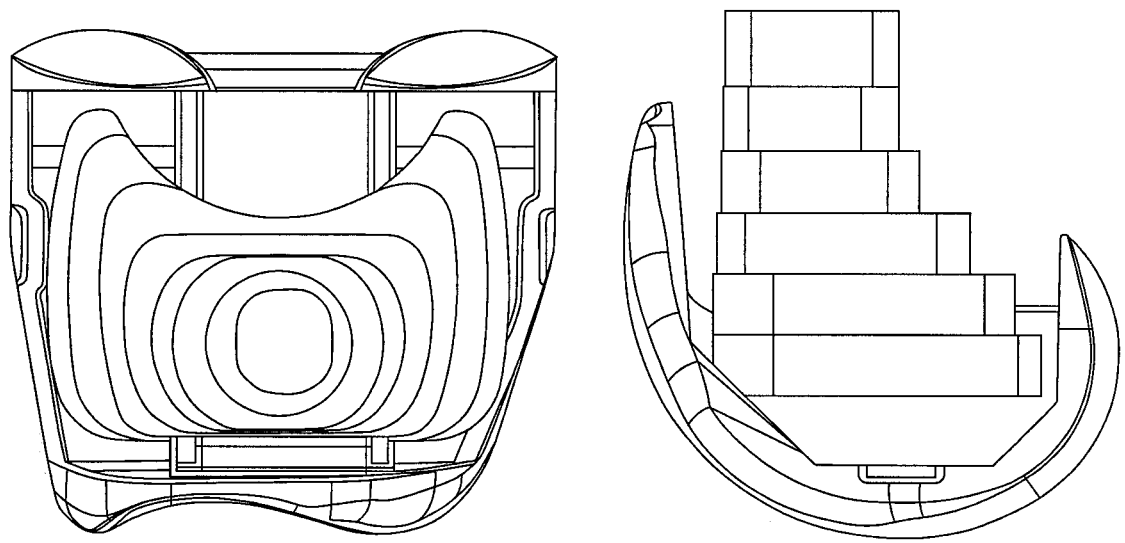
FIG. 4 shows an example of a femoral sleeve with TC3 femur

FIG. 4 shows a sleeve in combination with Total Condylar 3 (TC3 femur). When the term "TC3 femur" is used herein, it refers to DuPuy's brandname for articles generically referred to as "stabilized femur", "revision stabilized femur", or "varus valgus constrained femur".

The internal surface of the instant sleeves, in contrast to the outer surfaces, is relatively smooth and provides a substrate for cementation of femoral components. In some embodiments, the interior wall has a low coefficient of friction of 0.3-0.7. In contrast, in some embodiments, the outer surfaces of the device can have a coefficient of friction of 0.7-1.5.

Occasionally after removal of the defective femoral component, the cavitary or peripheral rim defects are only present on either the medial or lateral side of the femur. To avoid excessive bone loss the femoral sleeve can be offset medially or laterally. Such devices are essentially a "half sleeve" with the sleeve being eccentric in only a single side of the device.

The device can be formed of layers in which the geometry of each layer is formed to conform to the anatomy of the distal femur. In some embodiments, the most distal layers are substantially rectangular and become increasingly circular proximally. A distal notch can be removed from the sleeve to account for a posterior stabilized cam box. A substantially circular cut from the device to account for the inter-condylar notch present at the distal posterior aspect of the femur can be utilized.

Other aspects of the invention concern methods of forming femur implants comprising joining the femoral sleeve to the femoral component. In some embodiments, the joining involves attaching the femoral sleeve to the femoral component through a morse taper between the femoral component boss and the taper adapter internal channel. Some examples of fastening systems are described in U.S. Pat. No. 5,824,097, the disclosure of which is incorporated herein by example.

Figure 5:
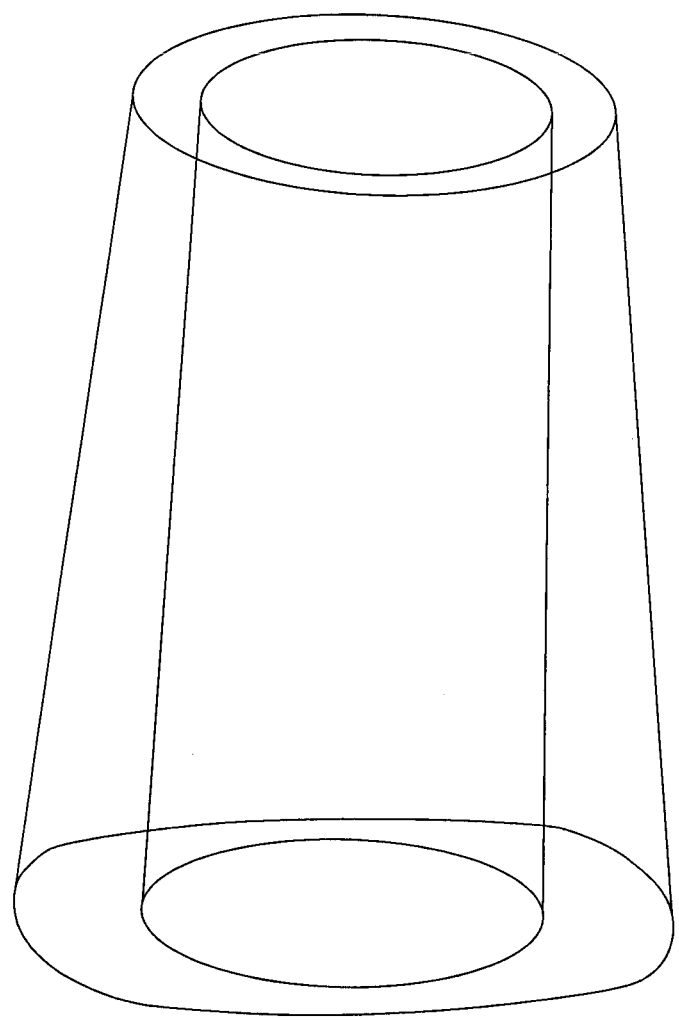
FIG. 5 shows an example of a taper adapter.

In some embodiments, the geometry of the femoral sleeve is such to be contained within the PFC Sigma TC3 femur as shown in FIG. 5.

The femoral sleeve includes a family of sleeves adapted to fit into the various sizes of TC3 femurs. The interior geometry of the sleeve is hollow to allow cementation of a femoral component and a stem extension. The femoral sleeve is placed into the distal femur and provides a platform for attaching a femoral component with distal augments. The femoral sleeve is configured in a manner to allow a 10 mm or 15 mm distal augment to be used with the femoral component. The sleeve geometry is optimized for use with a TC3 femur but would also function with other femur geometries.

Figure 6:
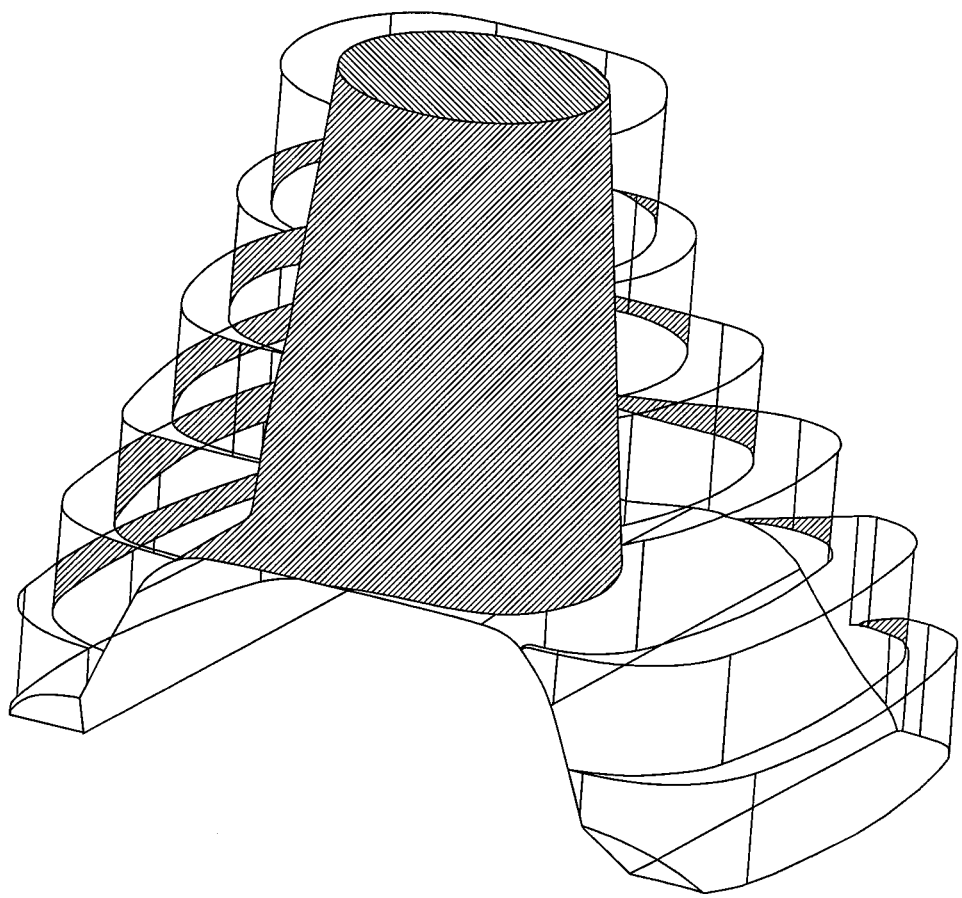
FIG. 6 presents an example of a femoral sleeve with a taper adapter.

Another embodiment of the femoral sleeve incorporates a taper adapter that is press-fit and sintered to the titanium foam sleeve. This embodiment allows superior cementless fixation to the distal femur while providing a rigid mechanical lock between the sleeve and the femur. Current DePuy femoral sleeves are attached to the TC3 femur through the use of the femoral adapter. The attachment method for the porous titanium sleeves would be identical to that of the current DePuy revision sleeves. FIG. 5 shows the taper adapter and FIG. 6 shows the assembly of the taper adapter and the porous titanium sleeve.

Figure 7:
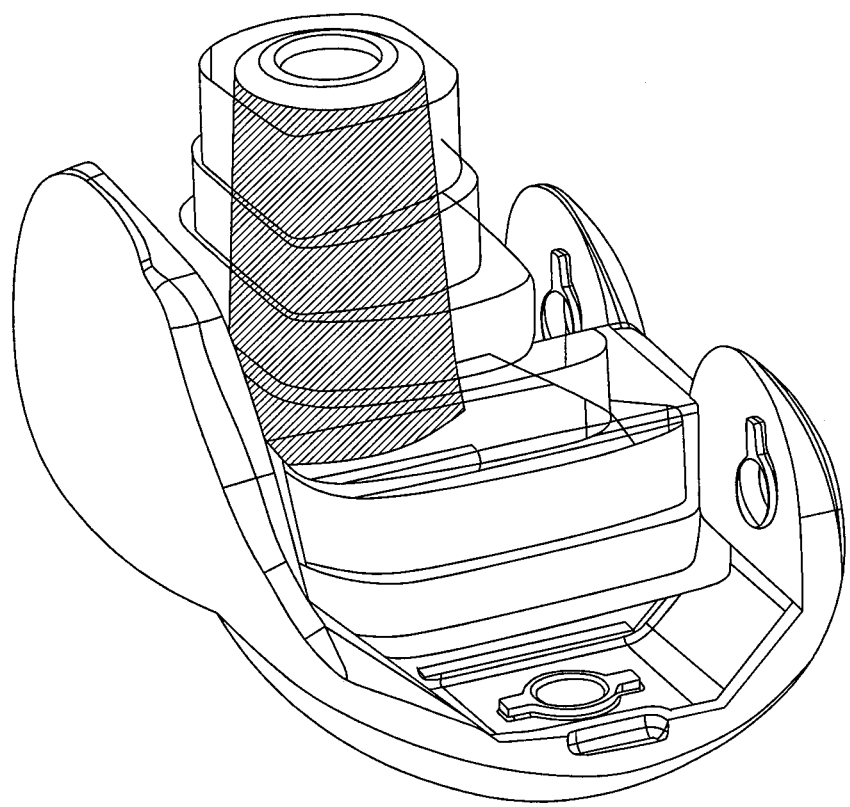
FIG. 7 shows an example of a TC3 femur with sleeve and taper adapter, anterior-medial.
Figure 8:
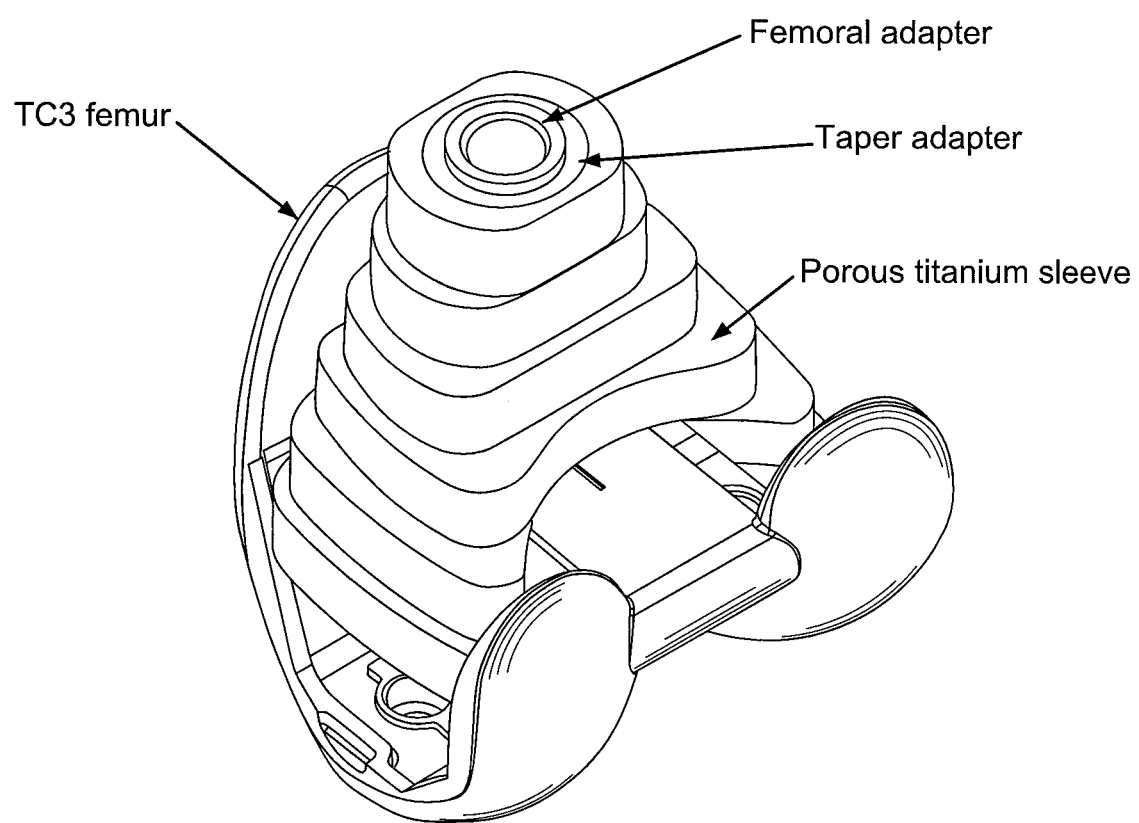
FIG. 8 presents an example of a TC3 femur with sleeve and taper adapter, posterior-medial.

The sleeve/taper assembly can be mechanically fixed to the TC3 femur through the use of the femoral adapter as shown in FIGS. 7 and 8.

Figure 9:
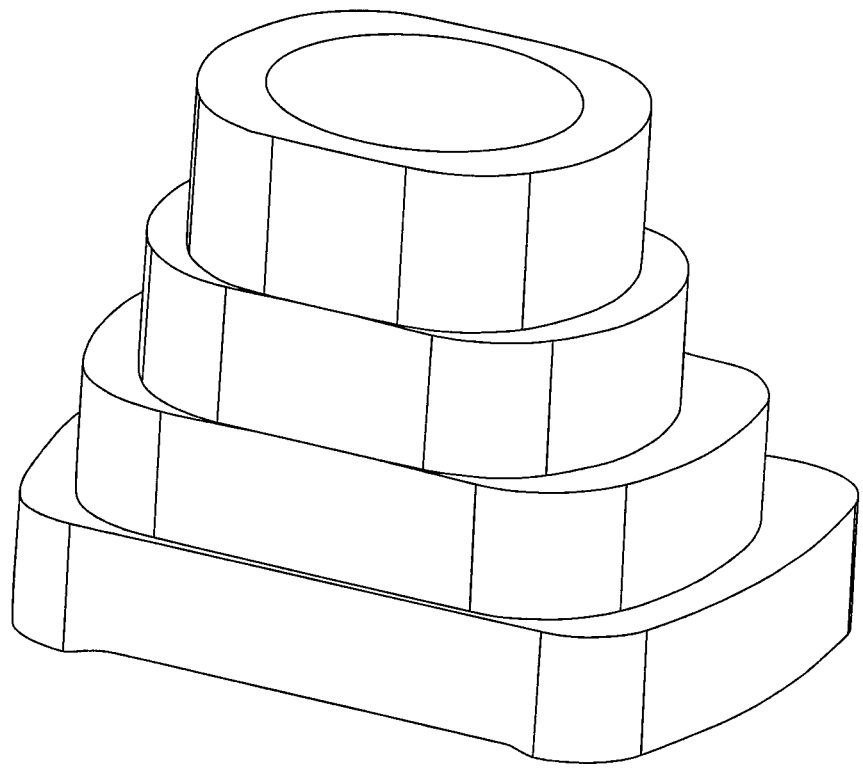
FIG. 9 shows an example of a femoral sleeve.
Figure 10:
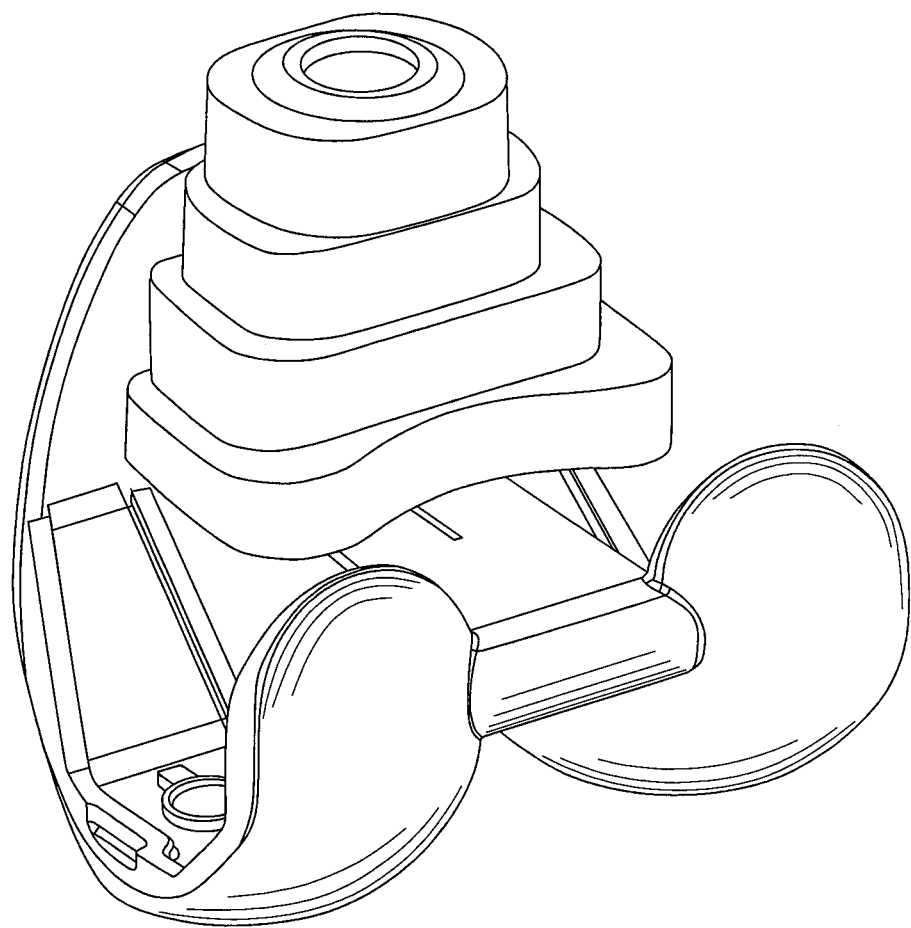
FIG. 10 presents an example of a femoral sleeve with taper adapter and TC3 femur.
Figure 11:
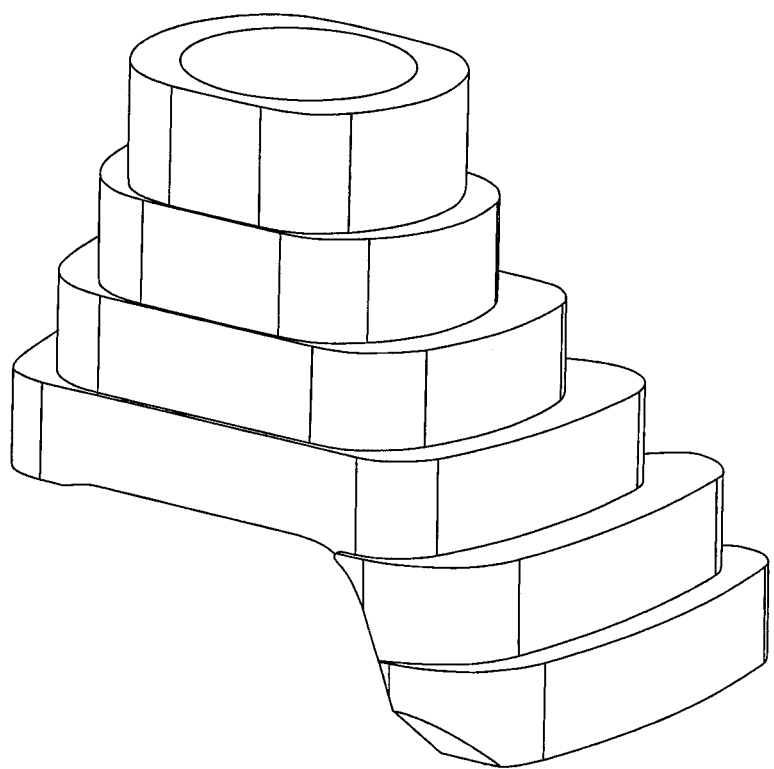
FIG. 11 presents an example of a femoral sleeve modified to fill a bone with a medial defect only.

Other aspects of the design are illustrated by FIG. 9 which shows one example of a tapered femoral sleeve. FIG. 10 presents an example of such a femoral sleeve with taper adapter and TC3 femur. FIG. 11 presents an example of a femoral sleeve modified to fill a bone with a medial defect only.

Figure 12A:
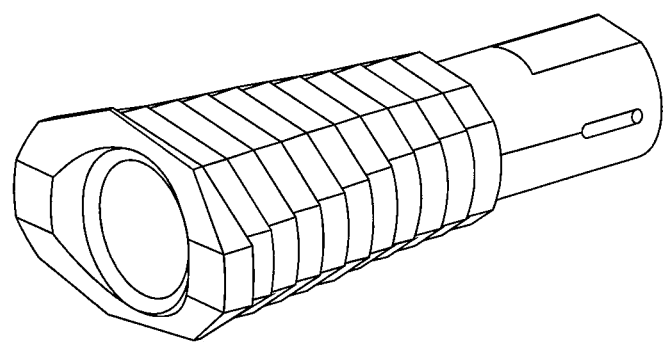
FIGS. 12 A-C present alternate geometries of femoral sleeves.
Figure 12B:
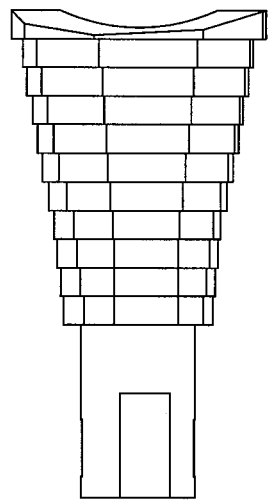
Figure 12C:
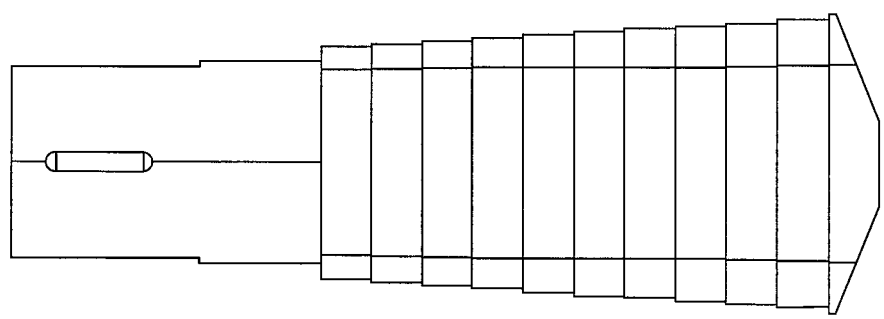
Figure 13:
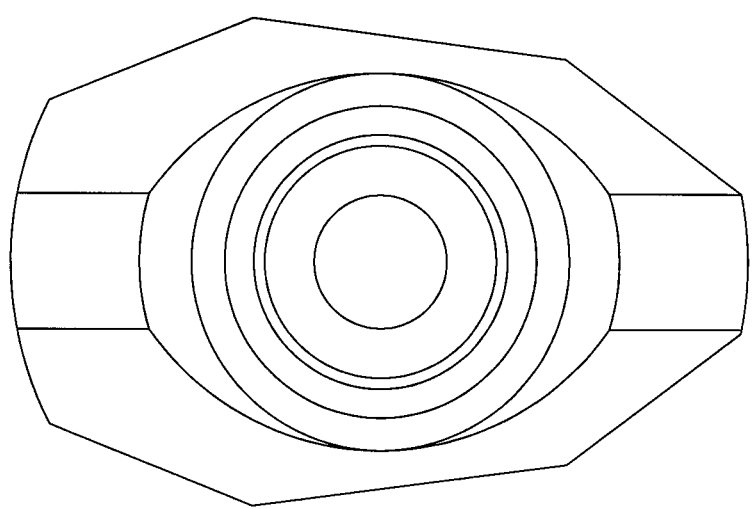
FIG. 13 shows an embodiment whose geometry provides a more polygonal shape in the outer surface's most distal layers and becomes increasingly circular proximally.

FIGS. 12 A-C and 13 show an embodiment where the terraced outer surface's most distal layers are substantially polygonal and become increasingly circular proximally. One skilled in the art can recognize other polygonal variations.

Figure 14A:
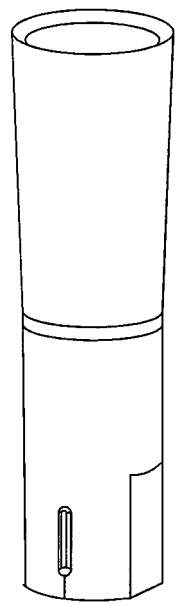
FIGS. 14 A and B present a taper adapter that in smaller in thickness compared to those shown in FIG. 5.
Figure 14B:
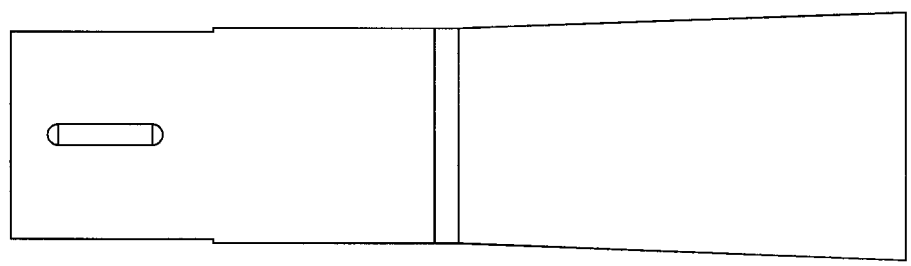

FIGS. 14 A and B show taper adapters that have smaller thickness than the design presented in FIG. 5. This design can be varied as needed for a particular sleeve or implant need.

The sleeves of the instant invention use highly porous Ti or Ti alloy constructs that have a rough outer surface. The rough surface has an open cell structure for making cancellous bone implants and cell and tissue receptors. This structure has been found to be superior to other porous metallic implant materials whose "porosity" is artificially produced via some form of surface treatment that does not result in a truly complete, open porosity. However, without any further treatment such implant surfaces typically are not sufficiently rough and such a surface roughness is an important structural property for initial stability of cementless fixation devices.

The outer surface of the sleeve can be roughened by conventional salt or sand blasting. Such methods are commonly used to induce a macro surface roughness. In such blasting, the surface may be exposed to a high velocity stream of salt or sand that physically gouges away parts of the surface. Depending on the conditions used, at least the outer 10 or 20 microns are impacted by the process. In the case of salt blasting, residual salt can be removed by an aqueous rinse. Conventional machining or glass bead blasting are typically not the method of choice due to its high porous nature with the open cell structure of the implants. Glass fragments can become intraped and present issues after implant. Traditional machining can reduce the porosity of the surface.

In some embodiments, the inner channel is not subjected to salt or sand blasting and is not as rough as the outer surface. In certain embodiments, the inner surface is smoothed by inserting a metal insert with a relatively smooth surface into the interior channel. The interior channel can also be mechanically smoothed by a grinding, burnishing, blasting, or spraying process to create a surface capable of mating with the boss of the femoral component. Because porosity is more important to the outer surface (for bone ingrowth) than the inner channel, any loss of porosity by this process is not as important as a loss at the outer surface.

The Ti or Ti alloy foams can be made, for example, by conventional techniques that mix Ti or Ti alloy powder with a pore-foaming agent (PFA). The powder mixture can be compacted under high pressure to form green bodies. The PFA can be removed from the green body which can then be sintered to form to article.

The Ti or Ti alloy powder also can be present in a wide variety of particle sizes and particle size distributions. Certain preferred particle size ranges are from about 20 μm to about 100 μm, from about 25 μm to about 50 μm, and from about 50 μm to about 80 μm.

The term "CP titanium" refers to commercially pure titanium which is well known to those skilled in the art. CP titanium is an unalloyed titanium. Typically, CP titanium contains over 98% pure titanium.

The term "pore forming agent" refers to a material that can be mixed with a metal powder and removed after the mixture is compacted. Such materials are also known in the art as "pore forming" materials. In some embodiments, the pore forming agents are be removed by a liquid. Suitable liquids include aqueous solutions and water. Pore forming agents include water soluble salts such as sodium chloride, potassium chloride, lithium chloride, potassium sorbate, sucrose, or mixtures thereof After the extractible particulates are removed, the extraction agent or solvent can be removed via evaporation optionally using heat and/or vacuum.

The pore forming agent (PFA) can be present in a wide variety of particle sizes and particle size distributions suitable to produce a desired pore size and pore size distribution. Certain preferred particle size ranges are from about 200 μm to about 600 μm, from about 200 μm to about 350 μm, and from about 350 μm to about 550 μm. Those skilled in the art will recognize that the proportions of metal powder and PFA will vary depending upon the type of structure sought to be produced. In certain embodiments of the present invention, the ratio of metal powder to PFA is about 40:60 to about 10:90.

After treatment to remove the PFA, the green body typically consists of a metal skeleton, which can be subsequently bonded together through high-temperature sintering process to produce Ti or Ti alloy foams with highly porous structures.

Metal powder and PFA are weighed and their respective densities are used to find the volume of each. These values are used to calculate the volume porosity of the mixture, which is generally given with respect to the PFA. Porosity can be determined by measuring the weight of a sintered sample and calculating its volume using the following formula:

% Porosity=weight/(density of solid metal*volume)*100.

Porosity can also be determined by analyzing cross-section images. Images are taken of mounted, polished cross-sections of the metal foam material. The metal reflects the light and appears white, while the pores appear black.

The mixtures of metallic powder and pore forming agents can be compacted by uniaxial compacting, multi-axial compacting, or isostatic compacting. The method of compacting each layer of the multilayer article can be selected independently. In some embodiments, the preferred method of compacting is cold isostatic press (CIP).

Sintering techniques are well known to the skilled artisan. In some embodiments, the sintering can be conducted in a temperature range that is about 1000 to 1400° C.

The implant can be cleaned prior to any process step or implantation. The cleaning can be performed, for example, with detergent, deionized (DI) water, and ultrasonic bath in 100% alcohol. Such treatment can be useful in removing grease and dust. Sometimes, it may be desirable to dry the implant in an oven after such cleaning.

Another method of cleaning the article is water jet cleaning (at a pressure of 3000 psi, for example) which can remove any weak connections on the surface pores that might otherwise fall off as debris when the implant surface is subjected to friction such as rubbing.

The cleaned implant can be subjected to heat treatment. In some embodiments, the treatment is at a temperature of at least 800° C. This step typically removes volatile impurities such as titanate residue.

The femoral sleeves of the instant invention offer combination of advantages not found in the art. These advantages include (1) stress transferring steps of porous titanium to optimize stress transfer and bone ingrowth, (2) a geometry optimized to minimize bone loss, (3) a variation of porous titanium surface roughness optimized for contact with bone, titanium or bone cement, and (4) highly porous sleeve optimized to fill either a medial or lateral defect without sacrificing good bone.

The invention is illustrated by the following examples that are intended to be illustrative but not limiting.

EXAMPLE 1

A rubber mold is created with a void approximately the shape of the femoral sleeve. A titanium powder/salt powder mixture is placed into the mold. A metal mandrel is placed into the mold and power mixture creating the interior channel of the sleeve. The mold and mandrel assembly is then placed into the isostatic press and compacted into solid form. The solid form is machined to form the final exterior terrace profile. The solid form is immersed in reverse osmosis water to remove the major portion of salt. The taper adapter is press-fit into sleeve. The entire assembly is sintered and entire part shrinks by approximately 13%.

EXAMPLE 2

Example 1 is performed using commercial pure titanium powder (Phelly Materials, Inc. Bergenfield, N.J., USA) particle size: 45-75 μm and NaCl (Fisher Scientific International Inc. Hampton, N.H., USA) particle size: 250-425 μm. The titanium and salt are mixed in a ratio of approximately 25:75 Ti:PFA by volume. The mixture is added to a mold and compressed into a green body at a compaction pressure of 22 ksi. The green body is placed in a water bath until the NaCl dissolved. The resulting metal skeleton is dried at 65° C. for 4 hours, and then sintered at 1204° C. for 2 hrs. A highly porous femoral sleeve results.

EXAMPLE 3

The femoral sleeve from Example 2 is joined to a femoral component by attaching the femoral sleeve to the femoral component through a morse taper between the femoral component boss and the taper adapter internal channel.

What is claimed:

1. A method of forming a femur implant comprising joining a femoral component including a pair of condyle surfaces and a cam box to a femoral sleeve assembly, the femoral sleeve assembly comprising:
    a monolithic foam femur sleeve, said femur sleeve comprising titanium or titanium alloy foam having a porosity of 50 to 85% and possessing: a proximal end, a distal end, an interior wall that defines an interior channel and extends from the proximal end to the distal end, a terraced outer surface that tapers such that said sleeve is widest at the distal end and most narrow at the proximal end, and a distal notch defined in the distal end, the distal notch extending from anterior to posterior and receiving the cam box of the femoral component,
    a titanium insert that has a porosity of less than 10% and is positioned within said sleeve such that a portion of the titanium insert is exposed within said outer surface, and
    a femoral adapter that is affixed to the titanium insert, the femoral adaptor having a channel extending therethrough.

2. The method of claim 1, wherein said sleeve has a porosity of 60 to 80%.

3. The method of claim 1, wherein the shape of the terraced outer surface generally corresponds to the shape of the distal end of the femur of a mammal.

4. The method of claim 1, wherein the titanium alloy is Ti6Al4V.

* * * * *